(12) United States Patent
Havelund

(10) Patent No.: US 6,635,617 B1
(45) Date of Patent: Oct. 21, 2003

(54) INSULIN PREPARATIONS FOR PULMONARY DELIVERY CONTAINING MENTHOL

(75) Inventor: Svend Havelund, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/418,778

(22) Filed: Oct. 15, 1999

Related U.S. Application Data

(60) Provisional application No. 60/106,018, filed on Oct. 28, 1998.

(30) Foreign Application Priority Data

Oct. 16, 1998 (DK) .......................................... 1998 01326

(51) Int. Cl.$^7$ ............................................. A61K 38/28
(52) U.S. Cl. ................................ 514/3; 514/4; 514/12; 530/303; 530/304
(58) Field of Search ................................ 530/303, 304; 514/3, 4

(56) References Cited

U.S. PATENT DOCUMENTS

| | | | |
|---|---|---|---|
| 5,474,978 A | 12/1995 | Bakaysa et al. ................ | 514/4 |
| 5,506,203 A | 4/1996 | Backstrom et al. ............ | 514/4 |
| 5,743,250 A | 4/1998 | Gonda et al. .......... | 128/200.14 |
| 5,747,445 A | 5/1998 | Backstrom et al. ............ | 514/4 |
| 6,017,545 A | * 1/2000 | Modi ........................ | 424/400 |

FOREIGN PATENT DOCUMENTS

| | | |
|---|---|---|
| EP | 0 692 489 A1 | 1/1996 |
| WO | WO 96/40089 | 12/1996 |
| WO | WO 97/48413 | 12/1997 |
| WO | 9811867 | * 3/1998 |
| WO | WO 98/42368 | 10/1998 |

OTHER PUBLICATIONS

Jens Brange, Stability of Insulin, Kluwer Academic Publishers pp. 6–128 (1992).
Brader et al., Biochemistry, vol. 30, pp. 6636–6645 (1991).
Galloway et al., Diabetes Care, vol. 4, pp. 366–376 (1981).
Bloom et al., J. Mol. Biol., vol. 245, pp. 324–330 (1995).
Derewenda et al., Nature, vol. 338, pp. 594–596 (1989).
Wollmer et al., Biol. Chem. Hoppe–Seyler, vol. 368, pp. 903–911 (1987).
Choi et al., Biochemistry, vol. 32, pp. 11638–11645 (1993).
Brzovic et al., Biochemistry, vol. 33, pp. 13057–13069 (1994).
Brems et al., Protein Engineering, vol. 5, pp. 519–525 (1992).
Elliott et al., Aust. Paediatr. J., vol. 23, pp. 293–297 (1987).
Okumura et al., International Journal of Pharmaceutics, vol. 88, pp. 63–72 (1992).
F. Sundby, The Journal of Biological Chemistry, vol. 237, pp. 3406–3411 (1962).
Robert F. Service, Science, vol. 277, pp. 1199–1200 (1997).
Dodson et al., Phil. Trans. R. Soc. Lond. A, vol. 345, pp. 153–164 (1993).
Riechelmann et al., Arzneim.–Forsch./Drug. Res., vol. 47 (II), pp. 1034–1039 (1997).
Gaworski et al., Food and Chemical Toxicology, vol. 35, pp. 683–692 (1997).
Abstract of article by Nishino et al., American Journal of Respiratory and Critical Care Medicine, vol. 156, pp. 309–313 (1997).
Abstract of article by Jager et al., Chemical Senses, vol. 21, pp. 477–480 (1996).
Abstract of article by Laude et al., Pulmonary Pharmacology, vol. 7, pp. 179–184 (1994).
Abstract of article by Stimpfl et al., Chemical Senses, vol. 20, pp. 349–350 (1995).
Abstract of article by Nasel et al., Chemical Senses, vol. 19, pp. 359–364 (1994).
Abstract of article by Gal–Fuzy et al., Pharmazie, vol. 39, pp. 558–559 (1984).

* cited by examiner

*Primary Examiner*—Christopher S. F. Low
*Assistant Examiner*—David Lukton
(74) *Attorney, Agent, or Firm*—Reza Green

(57) ABSTRACT

A stable, aqueous insulin formulation suitable for pulmonary delivery is disclosed. The formulation has increased convenience for the patient and improved bioavailability of insulin.

20 Claims, No Drawings

INSULIN PREPARATIONS FOR PULMONARY DELIVERY CONTAINING MENTHOL

This application claims priority under 35 U.S.C. 119 of Danish application PA 1998 01326 filed Oct. 16, 1998, and of U.S. Provisional application No. 60/106,018 filed Oct. 28, 1998, the contents of which are fully incorporated herein by reference.

FIELD OF THE INVENTION

The present invention relates to stable, aqueous insulin formulations suitable for pulmonary delivery with increased convenience for the patient and improved bioavailability of insulin.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal.

In solution, the self-association pattern of insulin is a complex function of protein concentration, metal ions, pH, ionic strength and solvent composition. For the currently used soluble preparations containing U100 insulin, zinc ions, isotonic agent and phenolic preservative, the following equilibria must be considered:

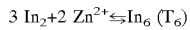

The known degradation patterns of insulin include a) fibril formation; b) deamidations at A18, A21 and B3; c) dimerisations via transamidation or Schiff-base formation; d) disulfide exchange reactions.

According to Brange (Stability of Insulin, Kluwer Academic Press, 1994), each of these degradation reactions proceed much faster in the monomeric state than in the hexameric state. Therefore, the most efficient means of stabilising insulin preparations is by pushing the above equilibrium as far to the right as possible. In addition to this general effect of mass action, the reactivity of selected residues is further modified depending on their direct involvement in the T→R conformational change. Thus, the reactivity of B3Asn is much lower in the R-state (when the residue resides in an α-helix) than in the T-state.

The interconversion between $T_6$, $T_3R_3$ and $R_6$ conformations of the two zinc insulin hexamer is modulated by ligand binding to the $T_3R_3$ and $R_6$ forms. Anions such as chloride have affinity for the fourth coordination position in the metal ions of $T_3R_3$ and $R_6$, while preservatives such as phenol binds to hydrophobic pockets located near the surfaces of the $T_3R_3$ and $R_6$ forms (Derewenda, Nature 338, 594, 1989 and, Brzovic, Biochemistry 33, 130557, 1994). By the use of $Co^{2+}$ insulin it has been shown that the combined effect of anion and phenol binding is particularly efficient in stabilising the $R_6$ state. (Brader, Trends Biochem. Sci. 30, 6636, 1991 and; Bloom, J. Mol. Biol. 245, 324, 1995).

Furthermore, for both $Zn^{2+}$- and $Co^{2+}$ insulin it has been shown that phenol is much more efficient than m-cresol in inducing R-state in the insulin hexamer (Woilmer, Biol. Chem. Hoppe-Seyler 368, 903, 1987 and, Choi, Biochemistry 32, 11638, 1993). High affinity phenol derivatives inducing R-state are 7-hydroxy-indol ((Dodson, Phil. Trans. R. Soc. Lond. A 345,153, 1993) resorcinol and 2,6- and 2,7-dihydroxy-naphtalen ((Bloom, J. Mol. Biol. 245, 324, 1995). The physical denaturation of insulin is known as fibrillation. In the fibrillar state extended peptide chains are laying parallel or anti parallel and hydrogen bonded to each other, so-called β-structure or β-pleated sheets. Fibrils represent usually the lowest state of energy of the protein, and only harsh conditions such as strong base may enable a regeneration from this state to the native state of correctly folded protein. Factors that promote the rate of formation of fibrils are increasing the temperature, increasing the surface area between the liquid and the air phase and, for zinc-free insulin, increasing the concentration. For hexameric zinc-insulin the rate of fibril formation decreases with increasing concentration. The formation of fibrils is believed to proceed via monomerization of insulin. Fibrils of insulin have the appearance of gels or precipitates.

Insulin derivatives having truncations in the C-terminal of the B-chain, e.g. despentapeptide (B26-B30) insulin and des-octapeptide (B23-B30) insulin are more prone to form fibrils than human insulin. Insulin analogues which dissociate readily from the hexameric unit to the monomeric form, e.g. the AspB28 human insulin and the LysB28-ProB29 human insulin, are likewise more prone to form fibrils than human insulin. The native state of insulin is stabilised by bringing about the conditions that stabilises the hexameric unit, i.e. the presence of zinc ions (2–4 zinc/hexamer), phenol (0.1–0.5% w/v) and sodium chloride (5–150 mM).

Addition of agents that reduce the surface tension at the air-liquid interface further reduces the propensity to fibril formation. Thus, polyethylene glycol, polypropylene glycol and copolymers hereof with an average molecular weights of about 1800 have found use as stabilisers in concentrated insulin solutions for infusion pumps (Grau, 1982. In: Neue Insuline (Eds. Petersen, Schlüter & Kerp), Freiburger Graphische Betriebe, pp. 411–419 and Thurow, 1981: patent DE2952119A1). For a comprehensive review on the physical stability of insulin see Brange 1994, Stability of Insulin, Kluwer Academic Publisher, pp. 18–23. Most of the chemical degradation of insulin in preparations is due to reactions involving the carboxamide function of the asparagine residues, in particular residues B3 and A21. Hydrolysis of the amide groups leads to desamido derivatives, and transamidation involving an amino group from another molecule leads to covalently linked dimers and, after similar consecutive reactions, to trimers and higher polymers.

In acid solution AsnA21 is the most reactive, leading to AspA21 insulin (Sundby, J. Biol. Chem. 237, 3406, 1962). In crude insulin of bovine and porcine origin, obtained by acid ethanol extraction, the most abundant dimers isolated were AspA21 -GlyA1 and AspA21-PheB1 linked (Helbig 1976, Insulindimere aus der B-Komponente von Insulinpr äparationen, Thesis at the Rheinisch-Westfälischen Technischen Hochschule, Aachen).

In neutral solution, which is the preferred embodiment of insulin preparations for injection therapy, AsnB3 is the most susceptible residue. Degradation products include AspB3 insulin, AspB3-GlnB4 isopeptide insulin, and dimers and higher polymers where AspB3 provides the carbonyl moiety of a peptide bond with an amino group of another molecule.

For a comprehensive review on the chemical stability of insulin see Brange 1994, Stability of Insulin, Kluwer Academic Publisher, pp. 23–36. As for the physical stability conditions that stabilises the hexameric unit, i.e. the presence of zinc ions (2–4 zinc/hexamer), phenol (0.1–0.5% w/v) and sodium chloride (5–150 mM), decrease the rate of formation of degradation products during storage at neutral pH.

A different type of polymerisation reaction is observed when the conditions that stabilises the hexameric unit is neglected. Thus, in the absence of zinc, phenol and sodium chloride, and using a temperature of 50° C., disulfide-linked dimers and high molecular weight polymers are the prevailing products formed. The mechanism of formation is a disulfide interchange reaction, resulting from β-elimination of the disulfides (Brems, Protein Engineering 5, 519, 1992).

Solubility of insulin is a function of pH, metal ion concentration, ion strength, phenolic substances, solvent composition (polyols, ethanol and other solvents), purity, and species (bovine, porcine, human, other analogues). For a review see Brange: Galenics of Insulin, Springer-Verlag 1987, p.18 and 46.

The solubility of insulin is low at pH values near its isoelectric pH, i.e. in the pH range 4.0–7.0. Highly concentrated solutions of porcine insulin (5000 U/ml~30 mM) have been brought about at acid pH (Galloway, Diabetes Care 4, 366, 1981), but the insulin in the formulation is highly instable due to deamidation at AsnA21. At neutral pH highly concentrated solutions of zinc free insulin can be made, but these are unstable due to a high rate of polymerisation and deamidation at AsnB3. Porcine zinc insulin solutions at neutral pH comprising phenol have been reported physical stable at concentrations of 1000 U/ml at elevated temperature, but become supersaturated when the temperature is lowered to 4° C. (Brange and Havelund in Artificial Systems for Insulin Delivery, Brunetti et al. eds, Raven Press 1983).

In order to reduce the inconvenience of insulin injections much attention has been given to alternative routes of administration (for an overview see Brange and Langkjaer in Protein Delivery: Physical Systems, Sanders and Hendren, eds., Plenum Press 1997). Pulmonary delivery seems to be the most promising of these (Service, Science 277, 1199.1997). Insulin can be given aerolised in the form of dry powder or as nebulised droplets from an insulin solution. The efficacy might be enhanced by coached breathing (Gonda, U.S. Pat. No. 5,743,250) and addition of an absorption enhancer (Baekstroem, U.S. Pat. No. 5,747,445) or protease inhibitors (Okumura, Int. J. Pharm. 88, 63, 1992).

The bioavailability of a nebulised concentrated insulin solution (500 U/ml) was shown to be 20–25% as compared to a subcutaneous injection (Elliot, Aust. Paediatr. J. 23, 293, 1987). By using 30–50 μl insulin solution per puff the insulin solution need to be 5–20 times more concentrated than the usual concentration of 0.6 mM. By using a single dose container, e.g. a blister pack (Gonda, U.S. Pat. No. 5,743,250), the demand for a preservative is abolished. Most insulin formulations are preserved by the toxic, mucose irritating and unpleasant odorous phenol and m-cresol. However, omitting phenols will cause stability problems. In addition to the bacteriostatic efficacy, the phenols act as physico-chemical stabilisers of insulin in combination with zinc ions. So, it is preferred that formulations of insulin for inhalation are made with a minimum concentration of phenol or that phenol has been replaced by more acceptable substitutes.

DESCRIPTION OF THE INVENTION

Definitions

By "analogue of human insulin" (and similar expressions) as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" (and similar expressions) as used herein is meant human insulin or an analogue thereof in which at least one organic substituent is bound to one or more of the amino acids.

By "phenols" or "phenolic molecules" as used herein is meant phenol or derivatives thereof such as m-cresol or chloro-cresol.

By "menthol" is meant (–)-menthol and derivatives thereof as well as racemic menthol.

BRIEF DESCRIPTION OF THE INVENTION

It is an object of the present invention to provide an insulin formulation for pulmonary delivery which has an increased convenience for the patient without deteriorating its physical and chemical stability.

It is also an object of the invention to provide a pulmonary insulin formulation with an improved bioavailability of insulin.

Unexpectedly, these objects have been accomplished by providing an insulin formulation in which the amount of toxic and mucose irritating phenols has been minimized and in which menthol has been added.

Accordingly, the present invention relates to an aqueous insulin formulation comprising: human insulin or an analogue or a derivative thereof, 2 to 5 $Zn^{2+}$ ions per six molecules of insulin, 3 to 18 phenolic molecules per six molecules of insulin, and menthol.

The characteristic smell of menthol masks the presence of unpleasant phenols in the formulation and, surprisingly, the chemical and physical stability is not adversely affected by menthol.

Furthermore, the presence of menthol alleviates the sensation of respiratory discomfort associated with the act of inhaling, improve inspiratory and exspiratory volume, and mediates an antitussive effect.

Moreover, an increase in the bioavailability of insulin can be observed in comparison with formulations without menthol.

As an alternative to menthol, eucalypthol and related substances may be used according to the present invention. Furthermore, the smell might be adjusted by a mixture of these compounds.

Preferred Embodiments

The insulin formulation according to the present invention preferably comprises 0.5 to 4 mM of menthol.

The amount of phenolic molecules in the insulin formulation preferably corresponds to 4 to 9 phenolic molecules per six molecules of insulin, more preferably to about 6 phenolic molecules per six molecules of insulin.

The phenolic molecules are preferably selected from the group consisting of phenol, m-cresol, chloro-cresol, thymol, or any mixture thereof.

The insulin formulation preferably contains 0.3 to 20 mM, more preferably 0.6 to 15 mM, still more preferably 3 to 12 mM of human insulin or an analogue or a derivative thereof.

The stability of the insulin formulation is further improved when the concentration of chloride is kept below 50 mM, preferably below 30 mM, and more preferably in the range of 5 to 20 mM.

A remarkable stability of the insulin formulation is obtained when it comprises less than 10 mM of any anions other than chloride and acetate.

In a particular embodiment the insulin may comprise a low amount of phosphate buffer, preferably up to 5 mM of phosphate.

Insulin formulations of the invention comprising 2 to 4 $Zn^{2+}$ ions, preferably 2.2 to 3.2 $Zn^{2+}$ ions per six molecules of insulin, are very stable.

Insulin formulations of the invention comprising 3 to 5 $Zn^{2+}$ ions, preferably 3.5 to 5 $Zn^{2+}$ ions per six molecules of insulin, are also advantageous.

Surprisingly, it is possible to add a relatively high concentrations of zwitterions such as glycylglycine and glycine to the insulin formulation of the invention without decreasing the solubility of insulin. Glycylglycine act as buffer at neutral pH and furthermore increase the dissolution rate of zinc insulin at neutral to basic pH due to a moderately zinc chelating effect. Also, glycylglycine may act as a scavenger for amine reactions during the storage time. Thus, in a preferred embodiment the insulin formulation of the invention further comprises 5 to 150 mM of a zwitterionic amine, preferably glycylglycine or glycine.

In a preferred embodiment the insulin formulation of the invention further comprises 5 to 50 mM of trishydroxymethylaminomethan, which acts as a buffer at neutral pH and as a scavenger for amine reactive compounds.

In another preferred embodiment the insulin formulation of the invention comprises sodium ions as cations. The sodium ion has a low salting out effect.

In another preferred embodiment the insulin formulation of the invention comprises potassium or a mixture of potassium and sodium ions as cations. Potassium ions in a concentration higher than the plasma concentration of 4–5 mM increase the transport of insulin through the lungs.

In another preferred embodiment potassium ion in a concentration more than 4–5 mM is used in combination with a mild bronchodilator such as menthol.

In another preferred embodiment the insulin formulation of the invention comprises between 0.001% by weight and 1% by weight of a non-ionic surfactant, preferably tween 20 or Polox 188. A nonionic detergent can be added to stabilise insulin against fibrillation during storage and nebulisation.

In another preferred embodiment the insulin formulation of the invention comprises 1 mM to 10 mM of an anionic surfactant, preferably sodium taurocholate, in order to further increase the bioavailabilty of insulin.

In a preferred embodiment the insulin used is human insulin.

In another preferred embodiment the insulin used is an analogue of human insulin wherein position B28 is Asp, Lys, Leu, Val or Ala and position B29 is Lys or Pro; or des(B28-B30), des(B27) or des(B30) human insulin.

The preferred analogues of human insulin are those in which position B28 is Asp or Lys, and position B29 is Lys or Pro, preferably $Asp^{B28}$ human insulin or $Lys^{B28}Pro^{B29}$ human insulin.

In another preferred embodiment the insulin is selected from the group of soluble longacting insulin derivatives such as derivatives of human insulin having one or more lipophilic substituents, preferably acylated insulins.

The insulin derivative according to this embodiment is preferably selected from the group consisting of B29-$N^{\epsilon}$-myristoyl-des(B30) human insulin, B29-$N^{\epsilon}$-palmitoyl-des(B30) human insulin, B29-$N^{\epsilon}$-myristoyl human insulin, B29-$N^{\epsilon}$-palmitoyl human insulin, B28-$N^{\epsilon}$-myristoyl $Lys^{B28}Pro^{B29}$ human insulin, B28-$N^{\epsilon}$-palmitoyl $Lys^{B28}Pro^{B29}$ human insulin, B30-$N^{\epsilon}$-myristoyl-$Thr^{B29}Lys^{B30}$ human insulin, B30-$N^{\epsilon}$-palmitoyl-$Thr^{B29}Lys^{B30}$ human insulin, B29-$N^{\epsilon}$-(N-palmitoyl-$\gamma$-glutamyl)-des(B30) human insulin, B29-$N^{\epsilon}$-(N-lithocholyl-$\gamma$-glutamyl)-des(B30) human insulin, B29-$N^{\epsilon}$-($\omega$-carboxyheptadecanoyl)-des(B30) human insulin and B29-$N^{\epsilon}$-($\omega$-carboxyheptadecanoyl) human insulin.

The most preferred insulin derivative is B29-$N^{\epsilon}$-myristoyl-des(B30) human insulin or B29-$N^{\epsilon}$-(N-lithocholyl-$\gamma$-glutamyl)-des(B30) human insulin.

The above mentioned soluble long acting insulin derivatives bind albumin and have been designed to provide a constant basal supply of insulin (Markussen, Diabetologia 39, 281, 1996). Subcutaneous administration once or twice daily secure the required basal delivery of insulin, whereas several daily inhalations are recommended using pulmonary administration, preferably in connection with meals.

The insulin derivatives have a protracted onset of action and may thus compensate the very rapid increase in plasma insulin normally associated with pulmonary administration. By careful selection of the type of insulin, the present invention enables adjustment of the timing, and in order to obtain the desired insulin profile.

In a particular embodiment of the present invention, the insulin formulation comprises an insulin analogue or human insulin as well as an insulin derivative.

The insulin formulations of present inventions preferably has a pH value in the range of 7 to 8.5, more preferably 7.4 to 7.9 to ensure optimum stability.

This invention is further illustrated by the following examples which, however, are not to be construed as limiting. The term "Equivalent" is used as stoichiometric amount relative to insulin.

EXAMPLE 1

Human zinc insulin was dispersed in water (1:10 (w/w)) on icebath. After gentle stirring glycylglycine (7/15 equivalent) and sodium hydroxide (3.1 equivalent) were added and the mixture stirred slowly at 5° C. until the insulin was dissolved. 0.1 equivalent of zinc chloride and detergent was added. The pH was adjusted to 7.5 by 0.8 equivalent of hydrochloric acid and the volume adjusted before adding phenol (0, 0.67, 1, and 1.33 equivalent per insulin) or chlorcresol (1 equivalent) or cresol (1 equivalent), menthol (0, 1 and 2 mM from a stock solution of 1 M in ethanol), and water. Finally the 15 mM preparation was diluted with medium containing sodium chloride, glycylglycine, detergent, and menthol to obtain 12, 9, 6, and 3 mM of human insulin. (Table 1).

The odour of the solutions was evaluated by smelling directly over 1 ml of final solution of 9 mM of insulin. The smell of phenol was very weak at 0.67 equivalents of phenol per insulin and increasing to moderate at 1.33 equivalents. Adding 1 mM of menthol masked the smell of phenol at the 3 levels, and at 2 mM of menthol the mentholic odour was pronounced. 1 mM of menthol also masked the smell of 1 equivalent of chlorcresol per insulin. The smell of cresol was distinct at 1 mM of menthol and almost neutralised at 2 mM menthol.

The chemical stability of insulin was measured as the rate of covalent polymerisation. The polymerisation of insulin was not adversely affected by menthol.

The results are presented in the following Table 1.

TABLE 1

| Excipient 0.5 Zn²⁺/insulin, NaCl 15 mM glycylglycine 7 mM, tween 20 0.01%, pH 7.5 and: | Physical stability of solution at 5° C. Max. concentration without precipitation for 1 week. Test solutions were 3, 6, 9, 12, 15 mM insulin. | Chemical stability at 37° C. % polymer/week 3 mM insulin | 15 mM insulin |
|---|---|---|---|
| reference without phenols | 15 | 0.71 | 1.02 |
| 0.67 eqv phenol | 15 | 0.37 | 0.48 |
| 0.67 eqv phenol, 1 mM menthol | 15 | 0.42 | 0.47 |
| 0.67 eqv phenol, 2 mM menthol | 15 | 0.42 | 0.48 |
| 1 eqv phenol | 15 | 0.32 | 0.29 |
| 1 eqv phenol, 1 mM menthol | 15 | 0.32 | 0.30 |
| 1 eqv phenol, 2 mM menthol | 15 | 0.26 | 0.23 |
| 1.33 eqv phenol | 15 | 0.33 | 0.27 |
| 1.33 eqv phenol, 1 mM menthol | 15 | 0.27 | 0.21 |
| 1.33 eqv phenol, 2 mM menthol | 15 | 0.30 | 0.21 |
| 1 eqv cresol, 1 mM menthol | 15 | 0.45 | 0.38 |
| 1 eqv chloro-cresol, 1 mM menthol | 15 | 0.25 | 0.25 |
| 1 eqv phenol, 1 mM menthol, without tween 20 | 15 | 0.33 | 0.33 |
| 1 eqv phenol, 1 mM menthol, tween 20 replaced by Polox188 | 15 | 0.36 | 0.35 |
| phenol and cresol 16 mM | 15 | 0.22 | 0.19 |
| phenol and cresol 16 mM, menthol 1 mM | 15 | 0.24 | 0.18 |
| phenol and cresol 16 mM, menthol 2 mM | 15 | 0.24 | 0.19 |

What is claimed is:

1. A method for enhancing the bioavailability of human insulin or an analogue or derivative upon pulmonary administration, said method comprising:
providing an aqueous insulin formulation comprising: human insulin or an analogue or a derivative thereof, 2 to 5 $Zn^{2+}$ ions per six molecules of insulin, 3 to 18 phenolic molecules per six molecules of insulin, and menthol, wherein: (i) said insulin analogue or derivative exhibits insulin bioactivity, (ii) said insulin analogue comprises (a) human insulin in which one or more amino acids have been deleted and/or replaced by other amino acids or (b) human insulin containing at least one additional amino acid, (iii) said insulin derivative comprises human insulin in which at least one organic substituent is bound to one or more of the amino acids of said insulin; (iv) said phenolic molecules are selected from the group consisting of phenol, m-cresol, chloro-cresol, thymol, 7-hydroxyindole, 2,6-dihydroxynaphthalene, 2,7-dihydroxynaphthalene, and mixtures of any of the foregoing phenolic molecules and (v) said menthol increases the bioavailability of said insulin, analogue, or derivative following pulmonary administration.

2. The method according to claim 1, wherein said menthol is present at a concentration of 0.5 to 4 mM.

3. The method according to claim 1 comprising 4 to 9 phenolic molecules per six molecules of insulin.

4. The method according to claim 1, wherein the phenolic molecules are selected from the group consisting of phenol, m-cresol, chloro-cresol, and thymol.

5. The method according to claim 1, wherein said insulin, insulin analog, or insulin derivative is present at a concentration of 0.3 to 20 mM.

6. The method according to claim 1, wherein said formulation further comprises about 5–20 mM chloride ion.

7. The method according to claim 1, wherein said formulation further comprises up to 5 mM of phosphate ion.

8. The method according to claim 1, wherein said formulation comprises 2 to 4 $Zn^{2+}$ ions per six molecules of insulin.

9. The insulin formulation according to claim 1, having a pH value in the range of 7 to 8.5.

10. A formulation comprising (i) human insulin or an analogue or a derivative thereof, (ii) 2 to 5 $Zn^{2+}$ ions per six molecules of insulin, (iii) 3 to 18 phenolic molecules per six molecules of insulin, (iv) menthol, and (v) between 0.001% by weight and 1% by weight of a surfactant.

11. A formulation comprising (i) an analogue of human insulin, (ii) 2 to 5 $Zn^{2+}$ ions per six molecules of insulin, (iii) 3 to 18 phenolic molecules per six molecules of insulin, and (iv) menthol, wherein (a) said analogue comprises Asp, Lys, Leu, Val or Ala at position B28 and Lys or Pro at position B29; or (b) said analogue is des(B28–30), des(B27) or des(B30) human insulin.

12. The formulation according to claim 11, comprising an analogue of human insulin wherein the amino acid at position B28 is Asp or Lys, and/or the amino acid at position B29 is Lys or Pro.

13. A formulation comprising (i) a derivative of human insulin, (ii) 2 to 5 $Zn^{2+}$ ions per six molecules of insulin, (iii) 3 to 18 phenolic molecules per six molecules of insulin, and (iv) menthol, wherein said derivative of human insulin has one or more lipophilic substituents.

14. The insulin formulation according to claim 13, further comprising 5 to 150 mM of a zwitterionic amine.

15. The insulin formulation according to claim 13, further comprising 5 to 50 mM of trishydroxymethylaminomethane.

16. The insulin formulation according to claim 13, further comprising sodium ions, potassium ions, or a mixture of sodium ions and potassium ions.

17. The insulin formulation according to claim 13, wherein the insulin derivative is selected from the group consisting of B29-$N^{\epsilon}$-myristoyl-des(B30) human insulin, B29-$N^{\epsilon}$-palmitoyl-des(B30) human insulin, B29-$N^{\epsilon}$-myristoyl human insulin, B29-$N^{\epsilon}$-palmitoyl human insulin, B28-$N^{\epsilon}$-myristoyl $Lys^{B28}Pro^{B29}$ human insulin, B28-$N^{\epsilon}$-palmitoyl $Lys^{B28}Pro^{B29}$ human insulin, B30-$N^{\epsilon}$-myristoyl-$Thr^{B29}Lys^{B30}$ human insulin, B30-$N^{\epsilon}$-palmitoyl-$Thr^{B29}Lys^{B30}$ human insulin, B29-$N^{\epsilon}$-(N-palmitoyl-$\gamma$-glutamyl)-des(B30) human insulin, B29-$N^{\epsilon}$-(N-lithocholyl-$\gamma$-glutamyl)-des(B30) human insulin, B29-$N^{\epsilon}$-($\omega$-carboxyheptadecanoyl)-des(B30) human insulin and B29-$N^{\epsilon}$-($\omega$-carboxyheptadecanoyl) human insulin.

18. The insulin formulation according to claim 17, wherein the insulin derivative is B29-$N^{\epsilon}$-myristoyl-des(B30) human insulin or B29-$N^{\epsilon}$-(N-lithocholyl-$\gamma$-glutamyl)-des(B30) human insulin.

19. A method of administering insulin to a patient suffering from type I or type II diabetes, said method comprising administering by inhalation to said patient an insulin formulation comprising human insulin or an analogue or a derivative thereof, 2 to 5 Zn2+ ions per six molecules of insulin, 3 to 18 phenolic molecules per six molecules of insulin, and menthol, wherein: (i) said insulin analogue or insulin derivative exhibits insulin bioactivity, (ii) said insulin analogue comprises (a) human insulin in which one or more amino acids have been deleted and/or replaced by other amino acids or (b) human insulin containing at least one additional amino acid, (iii) said insulin derivative comprises human insulin in which at least one organic substituent is bound to one or more of the amino acids of said insulin; and (iv) said phenolic molecules are selected from the group consisting of phenol, m-cresol, chloro-cresol, thymol, 7-hydroxyindole, 2,6-dihydroxynaphthalene, 2,7-dihydroxynaphthalene, and mixtures of any of the foregoing phenolic molecules, and (v), said menthol increases the bioavailability of said insulin, insulin analogue, or insulin derivative following said administration.

20. The method according to claim 19, wherein insulin is administered at mealtime.

* * * * *